United States Patent [19]

Loboda

[11] 4,058,452

[45] Nov. 15, 1977

[54] ALKYLAROMATIC HYDROCARBON DEALKYLATION PROCESS

[75] Inventor: Robert S. Loboda, Hacienda Heights, Calif.

[73] Assignee: UOP Inc., Des Plaines, Ill.

[21] Appl. No.: 706,858

[22] Filed: July 19, 1976

[51] Int. Cl.² ............................................. C10G 35/04
[52] U.S. Cl. .................................. 208/134; 260/672 R
[58] Field of Search ...................... 260/672 R; 208/134

[56] References Cited

U.S. PATENT DOCUMENTS

| 3,306,841 | 2/1967 | Ward | 208/134 |
|---|---|---|---|
| 3,359,198 | 12/1967 | Lengemann | 260/672 R |
| 3,409,693 | 11/1968 | McHarg | 260/672 R |
| 3,445,536 | 5/1969 | DeGraff | 260/672 R |
| 3,691,059 | 9/1972 | Hallman | 260/672 R |

Primary Examiner—C. Davis
Attorney, Agent, or Firm—James R. Hoatson, Jr.; Robert W. Erickson; William H. Page, II

[57] ABSTRACT

A process for the dealkylation of alkylaromatic hydrocarbons wherein a hydrogen-rich gas stream passed through the reaction zone on a once-through basis is obtained by passing a hydrogen-containing feed gas stream into an absorber to remove light paraffins, and the gas separated from the reaction zone effluent by partial condensation is passed into a stripper as the stripping media used to remove these same light paraffins from the liquid used in the absorber. Processes for reforming and hydrotreating are also described.

7 Claims, 1 Drawing Figure

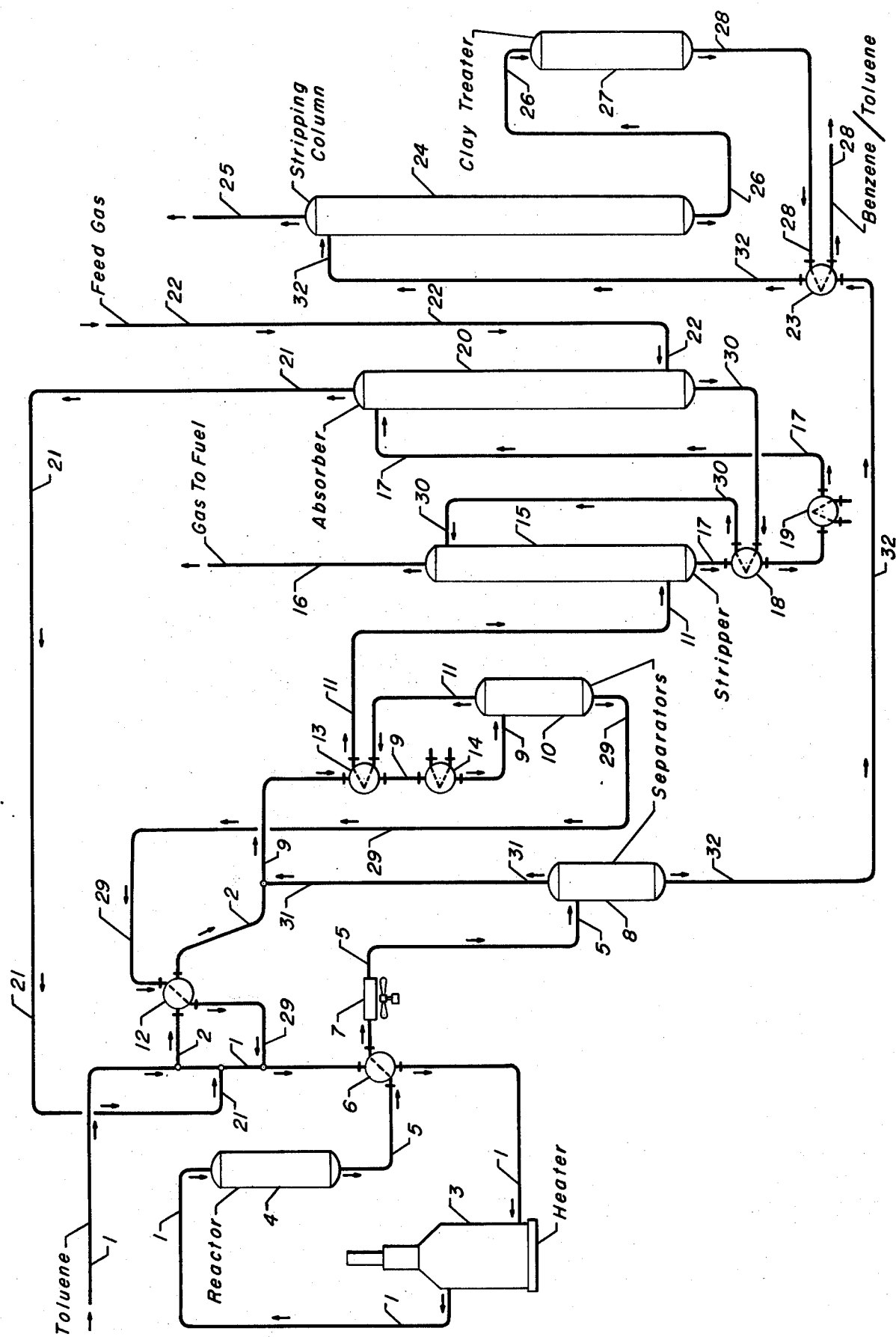

ALKYLAROMATIC HYDROCARBON DEALKYLATION PROCESS

FIELD OF THE INVENTION

The invention relates to a process for the conversion of mineral oils. More specifically, the invention relates to a process for the dealkylation of alkylaromatic hydrocarbons to produce benzene. This process may be either catalytic or noncatalytic, and the preferred feedstock is toluene. The invention also relates to processes for the reforming of naphthas and hydrotreating of various petroleum fractions.

PRIOR ART

Processes for the dealkylation of alkylaromatic hydrocarbons such as toluene are of commercial importance for the production of benzene. This results from the good demand for benzene for use in the production of styrene, phenol and alkylaromatic sulfonates such as surface active agents and detergents, etc. and the relatively low demand for toluene. These processes are of two basic types and are referred to herein as catalytic and thermal dealkylation depending on whether catalyst is used in the reactor.

A prior art process for thermal dealkylation is presented in U.S. Pat. No. 3,160,671 (Cl. 260-672). U.S. Pat. Nos. 3,284,526 and 3,291,849 also present processes for the thermal dealkylation of toluene. These references recognize that charging significant quantities of paraffinic hydrocarbons, such as butane, to the reaction zone is normally undesirable. The former reference deals with this problem by operating within certain temperature and residence time limits during the reactant preheating stage. The latter reference addresses the problem in a more pertinent manner by purifying the feed hydrogen in an absorber using part of the alkylbenzene feed as the lean oil. The resulting rich oil is then passed to an appropriate unit in the refinery for fractionation. This reference differs from the subject process in several ways. One of the most basic differences is that in the subject process the paraffinic hydrocarbons which were removed from the feed gas are rejected into the effluent gas stream. Furthermore, the effluent gas stream is beneficially used in the rich oil stripper as a stripping media. In comparison, no stripper is provided in the reference, and the hydrogen vent gas is shown as being vented without utilization as the stripping media. Other differences reside in the reaction zone effluent separation method which is used and in the preferred absorber oil recycling which eliminates the need to utilize a portion of the feed stream as the lean oil.

Catalytic dealkylation processes are described in U.S. Pat. Nos. 3,751,503; 3,197,523; 3,204,007 and 3,291,850 (all Cl. 260-672). These last two patents present typical flow schemes which includes a hydrogenrich recycle stream to the reaction zone. Both of them differ in that the off-gas stream of the vapor-liquid separation zone is passed into an absorber rather than into a stripper.

BRIEF SUMMARY OF THE INVENTION

The invention provides a process for the hydrodealkylation of alkylaromatic hydrocarbons in which paraffinic hydrocarbons are removed from a hydrogen-containing feed gas stream which is used on a once-through basis. The paraffinic hydrocarbons are removed from the feed gas stream in an absorber, and then the rich oil from the absorber is regenerated by stripping with the effluent gas of the process. The paraffinic hydrocarbons are thereby caused to bypass the reaction zone. Heat is supplied to the effluent gas used for stripping by heat exchange in the separator system which produces the effluent gas stream. This zone includes two vapor-liquid separation zones with intermediate cooling. The effluent gas stream is a cold gas stream produced in the second separation zone which is then heat exchanged against the gas stream produced in the first separation zone.

DESCRIPTION OF THE DRAWING

The drawing illustrates the preferred embodiment of the invention. It has been simplified for the purpose of clarity by the deletion of a large number of needed subsystems including controls, reboilers, overhead condensers, etc. This drawing and its description is not intended to limit the inventive concept to this exact mode of operation or exclude the other embodiments described herein.

In the preferred embodiment a liquid phase toluene stream enters the process through transfer line 1. A portion of this feed stream is diverted into line 2, and the remaining portion is admixed with a hydrogen-rich gas stream from line 21. This forms the basic reaction zone feed stream. To this stream is added a condensate stream carried in line 29. The reaction zone feed stream is then heat exchanged against the reaction zone effluent in exchanger 6 and passed through a fired heater 3. The resultant vapor stream is passed through the reaction zone 4 and removed as a vapor phase effluent stream carried by line 5. After heat exchange with the reaction zone feed stream it is partially condensed by an air cooler 7 and passed into a first vapor-liquid separator 8.

The first vapor-liquid separator is operated at conditions which promote an efficient division of the reaction zone effluent into a first separation zone gas stream removed in line 31 and a first condensate stream transferred through line 32. This condensate stream is passed into a product recovery zone after heat exchange in means 23. Preferably, this zone comprises a stripping column 24 from which light hydrocarbons are removed in line 25. The bottom product of the stripping column is passed through line 26 to a clay treater 27, and a product stream comprising benzene and toluene is removed from the process via line 28.

The first separation zone gas stream is cooled by admixture with the toluene flowing through line 2. This stream then continues through line 9 and is further cooled in heat exchanger 13 and by refrigeration in cooler 14. The resultant mixed phase stream is then passed into a second or cold vapor-liquid separator 10. The action and conditions in this separator produce a second condensate stream which is carried to a heat exchanger 12 to cool the diverted toluene and is then added to the reaction zone feed stream.

A second separation zone gas stream is carried from the second separator to the heat exchanger 13 and then to the stripper by line 11. Countercurrent contacting of this gas stream with a rich liquid stream entering the stripper 15 through line 30 results in the removal of $C_2$–$C_4$ paraffinic hydrocarbons from the rich liquid stream. This produces an off-gas stream comprising hydrogen and $C_2$–$C_4$ paraffinic hydrocarbons which is removed via transfer line 16. A lean stripping zone liquid effluent is removed in line 17 and heat exchanged against the rich liquid stream in means 18. It is then cooled by refrigeration in cooler 19 and charged to the top portion of absorber 20. This liquid descends countercurrently to the feed gas stream entering the process via line 22. $C_2$–$C_4$ paraffinic hydrocarbons are thereby transferred from the feed gas stream to a rich absorber liquid effluent removed in line 30. The unabsorbed gases are passed through line 21 and mixed with the toluene in line 1.

DETAILED DESCRIPTION

In a great many hydrocarbon conversion processes the hydrocarbon being processed is admixed with hydrogen prior to passage through a reaction zone. This is done for such reasons as to aid the vaporization of the hydrocarbon, to provide hydrogen which is necessary for the desired reaction or to prolong the life of catalyst used in the reaction zone. In many cases the hydrogen is recovered from the reaction zone effluent and recirculated. Often this recycle hydrogen stream is purified before being returned to the reaction zone. In a second mode of operation, referred to herein as "once-through" operation the hydrogen is not recycled, or if recycled it is only after having passed through other processing units or purification steps. This is most commonly practiced in processes which consume only minor amounts of hydrogen or which produce hydrogen. These include isomerization processes, alkylation processes, hydrogenation processes, reforming processes and mild desulfurization or denitrification processes. In its broadest embodiment the invention is applicable to these and other processes, in addition to the thermal dealkylation operation described herein, wherein it is desired to operate with a once-through hydrogen flow.

In its preferred embodiment the invention provides a process for the thermal dealkylation of alkylaromatic hydrocarbons, such as for the production of benzene from toluene. Toluene is produced in very large quantities in this country, often as the by-product of thermal cracking, extraction, reforming or isomerization operations, or directly from petroluem or coal derived naphtha fractions. However, the market for toluene is limited, and there is a significant economic incentive for its conversion to benzene since benzene is in demand as a basic starting material in the production of many petrochemicals.

As previously described, it has been recognized that it is undesirable to utilize a gas stream containing sizable amounts of normally vaporous $C_2$–$C_5$ paraffinic hydrocarbons as the hydrogen stream charged to a thermal dealkylation zone. For instance, these materials tend to crack into unsaturated hydrocarbons which consume hydrogen and cause the build up of coke within the reaction zone. In other processes these paraffinic materials may be undesirable because their presence lowers the hydrogen purity of the gas stream or because they interfere with the preferred reaction or increase the rate of side reactions. It is therefore an objective of this invention to provide a hydrocarbon conversion process utilizing a oncethrough hydrogen stream in which the concentration of $C_2$–$C_5$ paraffinic hydrocarbons is reduced from that of the feed gas stream. It is another objective of the invention to provide a process for the thermal dealkylation of alkylaromatic hydrocarbons.

These and other objectives are achieved by operation in a manner similar to that shown in the drawing. In accordance with this description the preferred embodiment of the invention may be characterized as a hydrocarbon conversion process which comprises the steps of passing a feed gas stream comprising hydrogen and $C_2$–$C_4$ paraffins through an absorption zone operated under conditions effective to remove $C_2$–$C_4$ paraffins, including countercurrent contact with a stripping zone liquid effluent stream, and thereby forming a hydrogen-rich gas stream and an absorption zone liquid effluent stream; passing the absorption zone liquid effluent stream into a stripping zone operated at conditions effective to cause the removal of $C_2$–$C_4$ paraffins from the absorption zone liquid stream, including countercurrent contact with a gaseous stripping media, and thereby forming the stripping zone liquid effluent stream and an off-gas stream comprising hydrogen and $C_2$–$C_4$ paraffins; admixing the hydrogen-rich gas stream with a hydrocarbon feed stream comprising toluene to form a reaction zone feed stream; passing the reaction zone feed stream through a thermal hydrodealkylation reaction zone as a vapor and thereby forming a reaction zone effluent stream; cooling and effecting a partial condensation of the reaction zone effluent stream and passing the reaction zone effluent stream into a first vapor-liquid separation zone operated at conditions effective to form a first condensate stream and a first separation zone gas stream; passing the first condensate stream into a product recovery zone; cooling and then passing the first separation zone gas stream into a second vapor-liquid separation zone operated at conditions effective to form a second condensate stream and a second separation zone gas stream; and, heating the second separation zone gas stream by indirect heat exchange against the first separation zone gas stream and passing the second separation zone gas stream into a lower portion of the stripping zone as the gaseous stripping media.

Effective conditions for the operation of the stripping zone and the absorption zone may be selected by those skilled in the art. Optimum conditions will depend on such factors as the composition of the feed gas stream, the liquid chosen for use as the absorption media and the degree of purification of the feed gas stream which is desired. A general range of conditions for the stripping zone include a pressure of from atmospheric to about 400 psig. or higher and a temperature of from about 100° F. to about 500° F. The absorption zone will be operated at a higher pressure or lower temperature or both in order to promote the absorption of the light hydrocarbons. The pressure utilized in this zone may range from about 100 psig. to 1000 psig. or higher, and the temperature may range from about 30° F. or lower to approximately 400° F. It is preferred that both zones comprise a single sieve tray contacting column, but any other suitable apparatus may also be employed. The preferred stripping media is $C_9$-plus aromatic hydrocarbons but any suitable material which is readily available may be utilized.

Conditions for use in the first and second vapor-liquid separation zones will also be dependent on variable factors, such as the composition of the material being processed. It is within the expertise of those skilled in the art to select a proper set of conditions. These may be any combination of temperature, pressure and flow rate which produces an effective separation of the reaction zone effluent stream into a gaseous stream and a liquid stream of the desired hydrocarbon product. A broad range of conditions include a temperature of from about 20° F. to 300° F. or higher and a pressure of about 100 psig. to about 1500 psig. Preferably, the second separation zone is operated at a pressure which is only slightly below that utilized in the first separation zone. This allows use of the pressure differential to cause the flow of the process streams without greatly interfering with the second separation operation. The second separation zone is therefore preferably operated at a pressure within about 25 psi. of the first separation zone. The temperature of the second separation is preferably 40 to 100 Fahrenheit degrees below that used in the first separation zone.

When the subject process is used for the thermal hydrodealkylation of alkylaromatic hydrocarbons, the reactor preferably comprises a vertical cylindrical vessel having an inlet at the top. This vessel will not contain any material chosen or designed to operate as a catalyst. Nevertheless, the materials used within the reactor may exhibit some minor amount of catalytic activity at the high temperatures utilized within this zone. This is unavoidable and is not considered in classifying the process. It is preferred that the upper one-half to two-thirds of the reaction zone be essentially empty and that the remaining lower portion of the zone contain a means for providing plug flow, such as inert ceramic balls, vertical baffles, etc. Thermal hydrodealkylation conditions include a temperature of from about 1100° F. to 1500° F. or higher and a pressure of from about 300 to about 800 psig. The residence time of the alkylaromatic hydrocarbon within the reaction zone should be within the broad range of from 4 to 60 seconds, with 12 to 30 seconds being a preferred range. A hydrogen to $C_6$-plus hydrocarbon ratio of at least 2 and preferably 4 to 8 is maintained within the reaction zone. The reaction zone should be operated in a manner which limits the temperature increase within the reaction zone to less than 200° F. and preferably within the range of from 100° F. to about 175° F.

Operating conditions in the reaction zone will vary according to the hydrocarbon conversion process in which the invention is being used. For instance, in the catalytic hydrodealkylation of alkylaromatics the preferred conditions include a pressure of from about 300 to 1000 psig. and a temperature of about 900° to 1500° F. One suitable catalyst for this process comprises an oxide of a metal of Group VI-B of the Periodic Table such as chromium, molybdenum or tungsten on a refractory inorganic oxide which is preferably alumina, but which may be an alumina-silica mixture, zirconia, etc. Other metals which may be utilized on the catalyst include those classified in Group VIII of the Periodic Table, including platinum, nickel, iron and cobalt and also rhenium and manganese. A particularly preferred catalyst comprises chrominum composited on a high surface alumina, such as gamma alumina, with the chromia being present in an amount of approximately 10 to 20 wt.% of chromium oxide based on the alumina. The feedstock should be charged at a liquid hourly space velocity in the range of from about 0.5 to about 5.0, with a hydrogen to hydrocarbon ratio of from 5:1 to about 15:1 being maintained in the reaction zone.

Other processes in which the invention may be practiced include the hydrotreating of various petroleum fractions for the removal of minor amounts of sulfur or nitrogen compounds, the hydrogenation of olefinic compounds and the reforming of $C_5$-$C_{12}$ hydrocarbons for the production of aromatic hydrocarbons or high octane gasoline blending components. For hydrotreating the reaction zone will contain a catalytically effective composite such as a metal selected from Groups VIII or VI-B of the Periodic Table or a combination of these metals. Again the catalyst is formed with an inorganic oxide support such as silica or alumina. A preferred catalyst comprises nickel and cobalt on an aluminasilica support. The alumina is preferably present in greater proportions, with the weight ratio of alumina to silica being from about 1.5:1 to 9:1, and preferably 1.5:1 to 3:1. This process is performed at a liquid hourly space velocity of about 1 to 5 at a pressure of about 100 to 1000 psig. and a temperature of from about 300° F. to 750° F. Hydrogen is circulated through the reaction zone at a rate of about 500 to 6,000 standard cubic feet per barrel of feed hydrocarbons. Further details on hydrotreating processes may be obtained by referring to such references as U.S. Pat. Nos. 3,537,982 and 2,767,121.

Reforming is typically performed on a naphtha at a temperature of from about 550° F. to about 1000° F., and preferably from 700° F. to 900° F. As used herein naphtha is intended to refer to a mixture of hydrocarbons, including some aromatic hydrocarbons, which boils between about 90° F. and 500° F. and preferably between 100° F. and 400° F. This process involves the vapor phase contacting of the feed material with a catalyst containing a platinum group metal in either a fixed bed or a moving bed reactor. The type of reaction zone employed may change the ranges of preferred conditions. For instance, a typical hydrogen to hydrocarbon mole ratio is about 10:1 with a fixed bed operation, but may vary from about 0.5:1 to 20:1. With a moving bed operation the catalyst the subject to frequent regeneration and lower hydrogen to hydrocarbon ratios of from 1:1 to 5:1 may be employed. The pressure utilized within the reforming reaction zone may vary from about 25 psig. to 1000 psig. or higher, but is preferably kept within the range of 50 psig. to about 200 psig. Generally, the liquid hourly space velocity may be from 0.5 to 10, with from 1.0 to 5.0 being a preferred range.

Reforming catalysts vary widely in their composition and in their method of manufacture, but almost universally contain one or more platinum group metals in an amount of from about 0.01 to 5 wt.% of the composite, with from about 0.10 to 0.80 wt.% being preferred. The preferred metal is platinum, but palladium, rhodium, ruthenium, etc. may also be employed. This metal is carried on an inorganic oxide support, which is preferably alumina spheres having a diameter of from about 1/16-inch to about ¼ -inch. The catalyst will preferably also contain a combined halogen such as chlorine, fluorine or iodine to impart a desired acid-acting character to the catalyst. This component is suitably present in the range of from 0.5 to about 1.5 wt.% of the composite when measured as the elemental halogen. The catalyst can also contain a promoter component. Typical promoters are rhenium, germanium, tin, lead and technetium. If used, this component is preferably present in an amount of from 0.1 to about 3.0 wt.% of the catalyst when measured as the elemental metal. As the subject invention is not centered on the composition of the catalyst used and suitable catalysts are available commercially, no further discussion is warranted. Further details of the reforming operation may be obtained by reference to U.S. Pat. Nos. 3,647,680; 3,821,104; 3,650,944; 3,830,727 and 3,647,679.

The invention is further illustrated by this example of the preferred embodiment. A feed gas stream of about 1968 mph (moles per hour) is passed into the bottom of an absorber having 24 trays at a temperature of about 92° F. This gas stream rises countercurrent to a lean liquid comprising mainly $C_9$ aromatics and some $C_{10}$ aromatics and lighter hydrocarbons. The lean liquid enters at a temperature of about 60° F., and the contacting is conducted at a pressure of about 545 psig. The lean oil has an average molecular weight of about 119.6 and a flow rate of approximately 776 mph. Of this about 720 mph comprises $C_9$ aromatics and about 39 mph is $C_{10}$ aromatics. The lean oil picks up about 11 mph of hydrogen, 27 mph of ethane, 65 mph propane, 36 mph of butanes and 14 mph of pentanes. The effluent gas stream of the absorber has a flow rate near 1811 mph, of which almost 1655 mph is hydrogen and 149 mph is methane and ethane.

A total toluene feed stream of about 223 mph is charged to the process. About 32 mph of this is diverted as the stream passed into the cold separator. This material is not lost as the liquid stream removed from the cold separator is added to the remaining portion of the feed stream. This stream comprises approximately 16 mph of benzene and 32 mph of toluene. The total feed stream to the reaction zone has a flow rate of about 2052 mph and is passed downward through a reaction zone of the preferred type as a vapor at a temperature of about 1240° F. and a pressure of about 448 psig.

The reaction zone effluent stream has a flow rate of about 2045 mph including 1410 mph of hydrogen and about 22 mph of toluene. This effluent stream is cooled from near 1395° F. to close to 600° F. by steam generation and heat exchanged against the combined feed stream. It is then further cooled to about 100° F. and passed into a first vapor-liquid separator operated at a pressure of about 385 psig. A 223 mph liquid stream is removed from the separator and passed into a 20-tray product stripper at the top tray. This stripper is operated with a bottom temperature of approximately 353° F. at about 120 psig. This effects the removal of small amounts of hydrogen, methane and ethane and produces a product stream of about 217 mph. This stream is then clay treated at about 350° F. It contains about 192 mph of benzene, 22 mph of toluene and 3 mph of bicyclic aromatics.

The vapor stream removed from the first vapor-liquid separator has a flow rate of about 1822 mph, of which approximately 1408 mph is hydrogen, 337 mph is methane and 58 mph is ethane. The toluene slipstream is admixed with this vapor stream, and the resulting admixture is passed into the cold separator at a temperature of approximately 40° F. at a pressure of about 371 psig. The liquid produced in this separation becomes part of the reaction zone feed stream after heat exchange against the toluene slipstream.

The vapor stream removed from the cold separator is passed into the bottom of a 24-tray stripping column at a temperature of about 160° F. This stripper is operated with a bottoms liquid temperature of about 235° 1 F. at a pressure of 53 psig. The rich oil produced in the absorber is fed onto the top tray of this stripper at a temperature of 160° F. and at a flow rate of about 934 mph. The hydrocarbons and hydrogen picked up in the absorber are rejected into the effluent gas from the cold separator. This produces a 1974 mph off-gas stream comprising hydrogen and $C_1$–$C_{10}$ hydrocarbons. A 12.4 mph absorber make up oil stream is added to the lean liquid removed from the stripper to replace the material lost overhead.

I claim as my invention:

1. A hydrocarbon conversion process which comprises the steps of:

a. passing a feed gas stream comprising hydrogen and $C_2$–$C_4$ paraffins through an absorption zone operated under conditions effective to remove $C_2$–$C_4$ paraffins, including countercurrent contact with a stripping zone liquid effluent stream, and thereby forming a hydrogenrich gas stream and an absorption zone liquid effluent stream;

b. passing the absorption zone liquid effluent stream into a stripping zone operated at conditions effective to cause the removal of $C_2$–$C_4$ paraffins from absorption zone liquid effluent stream, including countercurrent contact with a gaseous stripping media, and thereby forming the stripping zone liquid effluent stream and an off-gas stream comprising hydrogen and $C_2$–$C_4$ paraffins;

c. admixing the hydrogen-rich gas stream with a hydrocarbon feed stream to form a reaction zone feed stream;

d. passing the reaction zone feed stream through a reaction zone as a vapor and thereby forming a reaction zone effluent stream;

e. cooling and effecting a partial condensation of the reaction zone effluent stream and passing the reaction zone effluent stream into a first vapor-liquid separation zone operated at conditions effective to form a first condensate stream and a first separation zone gas stream;

f. passing the first condensate stream into a product recovery zone;

g. cooling and then passing the first separation zone gas stream into a second vapor-liquid separation zone operated at conditions effective to form a second condensate stream and a second separation zone gas stream; and, h. heating the second separation zone gas stream by indirect heat exchange against the first separation zone gas stream and passing the second separation zone gas stream into a lower portion of the stripping zone as the gaseous stripping media.

2. The process of claim 1 further characterized in that the hydrocarbon feed stream comprises toluene.

3. The process of claim 2 further characterized in that the reaction zone is substantially void of solids which would tend to catalyze the reaction, and in that the desired reaction is the thermal hydrodealkylation of toluene.

4. The process of claim 2 further characterized in that the reaction zone contains a bed of catalyst and in that the desired reaction is the dealkylation of toluene.

5. The process of claim 2 further characterized in that a portion of the hydrocarbon feed stream is admixed with first separation zone gas stream prior to the passage of the first separation zone gas stream into the second vapor-liquid separation zone.

6. The process of claim 5 further characterized in that the portion of the hydrocarbon feed stream admixed with the first separation zone gas stream is first cooled by indirect heat exchange against the second condensate stream, and in that the second condensate stream is then admixed with the reaction zone feed stream.

7. A process for catalytically reforming a naphtha which comprises the steps of:

a. passing a feed gas stream comprising hydrogen and $C_2$–$C_4$ paraffins through an absorption zone operated under conditions effective to remove $C_2$–$C_4$ paraffins, including countercurrent contact with a stripping zone liquid effluent stream, and thereby forming a hydrogenrich gas stream and an absorption zone liquid effluent stream;

b. passing the absorption zone liquid effluent stream into a stripping zone operated at conditions effective to cause the removal of $C_2$–$C_4$ paraffins from absorption zone liquid effluent stream, including countercurrent contact with a gaseous stripping media, and thereby forming the stripping zone liquid effluent stream and an off-gas stream comprising hydrogen and $C_2$–$C_4$ paraffins;

c. admixing the hydrogen-rich gas stream with a naphtha feed stream to form a reaction zone feed stream;

d. passing the reaction zone feed stream through a reaction zone as a vapor and thereby forming a reaction zone effluent stream;

e. cooling and effecting a partial condensation of the reaction zone effluent stream and passing the reaction zone effluent stream into a first vapor-liquid separation zone operated at conditions effective to form a first condensate stream and a first separation zone gas stream;

f. passing the first condensate stream into a product recovery zone;

g. cooling and then passing the first separation zone gas stream into a second vapor-liquid separation zone operated at conditions effective to form a second condensate stream and a second separation zone gas stream; and, h. heating the second separation zone gas stream by indirect heat exchange against the first separation zone gas stream and passing the second separation zone gas stream into a lower portion of the stripping zone as the gaseous stripping media.

* * * * *